Figure 3:
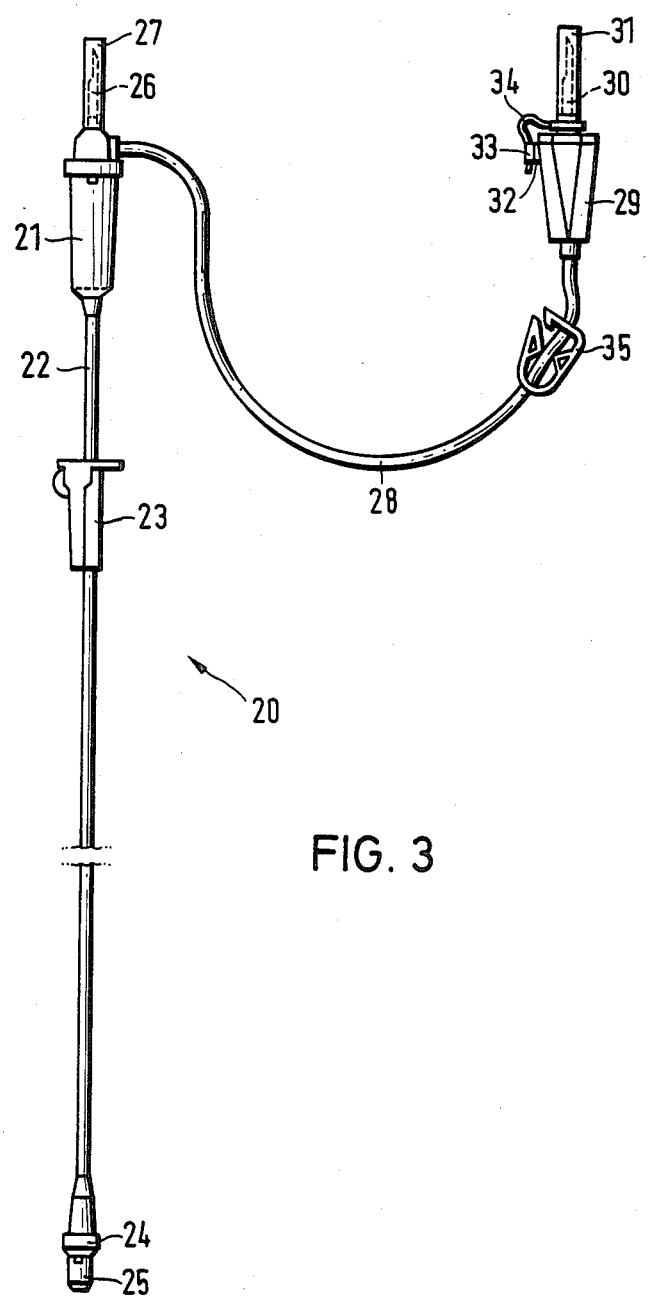

United States Patent [19]

Geisser et al.

[11] Patent Number: 4,715,851
[45] Date of Patent: Dec. 29, 1987

[54] MEANS FOR HANDLING TWO SOLUTIONS WHICH ARE TO BE MIXED TOGETHER

[75] Inventors: Peter Geisser, St. Gallen; Hans P. Kaiser, Zurich; Franz Berger, Gossau, all of Switzerland

[73] Assignee: Laboratorien Hausmann AG, St. Gallen, Switzerland

[21] Appl. No.: 872,863

[22] Filed: Jun. 11, 1986

[30] Foreign Application Priority Data

Jun. 25, 1985 [DE] Fed. Rep. of Germany ....... 3522645

[51] Int. Cl.$^4$ ........................ A61M 37/00; A61M 5/14
[52] U.S. Cl. ....................................... 604/82; 604/414
[58] Field of Search ..................................... 604/82–92, 604/414–416

[56] References Cited

U.S. PATENT DOCUMENTS

| | | | |
|---|---|---|---|
| 4,336,802 | 6/1982 | Stone et al. | 604/414 |
| 4,410,321 | 10/1983 | Pearson et al. | 604/82 |
| 4,600,040 | 7/1986 | Naslund | 604/415 |

Primary Examiner—C. Fred Rosenbaum
Assistant Examiner—H. Macey
Attorney, Agent, or Firm—Schwartz, Jeffery, Schwaab, Mack, Blumenthal & Evans

[57] ABSTRACT

The invention relates to a device for handling two liquids which are to be mixed together in a sterile manner directly before administration, to form an infusion solution to be administered parenterally, the apparatus comprising a first container in the form of a flexible bag made of plastics for receiving the one liquid and provided with a hanging member and a stopper closure, and a second container for the second liquid, which is likewise provided with a stopper closure, the two containers being held together and their interior spaces being capable of being put into communication with one another for the sterile mixing of the liquids contained in them. The second container is a rigid flask which can be closed in a vacuum-tight manner and has a volume corresponding to the volume of both liquids. A respective injection needle of an infusion set can be inserted through the stopper closures of each of the containers and has a ventable flexible connecting tube in order to connect the two containers together so that the negative pressure prevailing in the flask sucks the liquid from the flexible bag into the flask.

13 Claims, 6 Drawing Figures

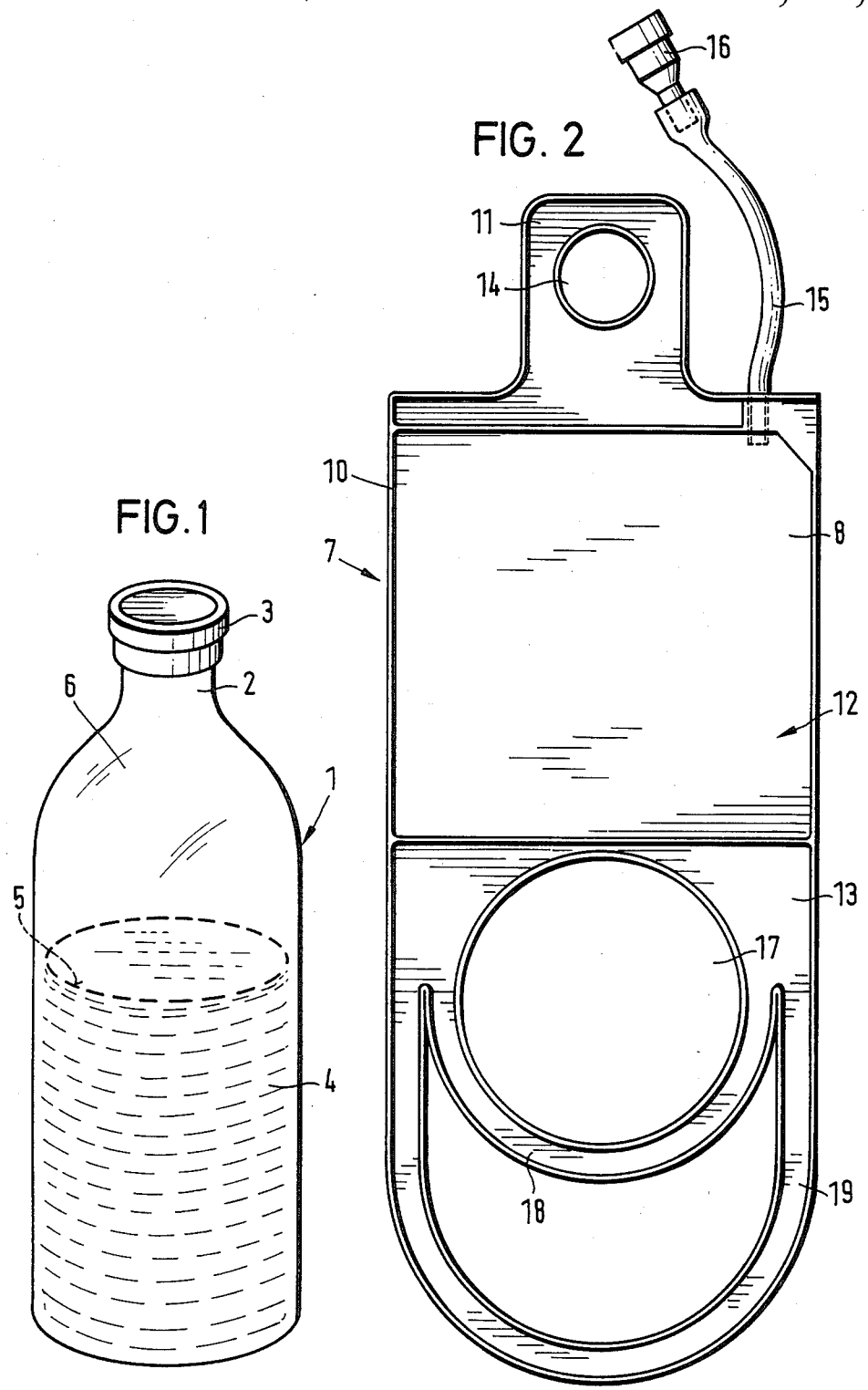

MEANS FOR HANDLING TWO SOLUTIONS WHICH ARE TO BE MIXED TOGETHER

The invention relates to means for handling two liquids which are to be mixed together in a sterile manner directly before administration, such as infusion solutions to be administered, comprising a first container in the form of a flexible bag made of plastics for receiving the one liquid, which is provided with hanging means and a stopper closure, and a second container for receiving the second liquid, which is likewise provided with a stopper closure, the two containers being held together and their interior spaces being capable of being put into communication with one another for the sterile mixing of the liquids contained in them.

It is often necessary that parenteral solutions to be administered, for example infusion solutions, should first be mixed together only directly before administration as on the one hand many mixtures do not maintain their condition over a long period and on the other hand it is frequently only decided by the doctor what mixtures are to be administered in the particular case.

Hitherto in such cases the two solutions have for example been administered separately. It is also known to store the two solutions in a double bag made of plastics, with two or more compartments for receiving the individual solutions, partitioned off by a rapturable connection (DE-3238649A1). Before administration the connection between the individual compartments of the container is torn open in order to be able to mix the liquids present in the compartments. For this purpose the bag must for example be squeezed by hand in order to achieve uniform mixing of the solutions, which is even then only achieved to a limited extent. Complete and thorough mixing can scarcely be obtained.

The separate administration of two solutions, just like the mixing of liquids contained in a double bag, requires mechanical steps which are expensive but do not lead to complete and uniform mixing. On the contrary, for example in the case of an infusion, there is the danger that the infusion bag can be ruptured by the mechanical mixing movement. Where glass connecting tubes are used there is also the danger that broken pieces of glass can get into the solution to be administered.

Some parenteral solutions to be administered cannot be stored in plastics containers and accordingly not in flexible plastics bags as an interaction can arise between the plastics material of the container or atmospheric oxygen penetrating through the plastics and the active components of the solution. This is true, for example, of amino acid solutions.

The aim of the invention is to provide means for storing two solutions completely separately and without the danger of any premature unwanted mixing, but which can be throroughly and uniformly mixed together before administration without the need for additional mechanical action.

This problem is solved according the to the invention by apparatus of the kind mentioned in the introduction in that the second container is a separate vacuum-tight closable rigid container having a volume corresponding to that of both liquids and that a respective injection needle of an infusion set can be inserted to the stopper closures of both containers the infusion set having a flexible connecting tube which can be vented and on one end of which there is one of the injection needles.

Thus the apparatus according to the invention comprises substantially three components, namely a flexible bag, a separate rigid container and a special infusion set with the aid of which the flexible bag and the rigid container can be put into mutual communication before the start of the administration, this infusion set serving not only to provide communication between the bag and the container but in addition it can be employed like an orthodox infusion set for administering the infusion solution. The vacuum-tight closable rigid container has a sufficiently large volume to accept the two solutions which are to be mixed together and to be delivered as a mixture, i.e. the liquid or solution present in the flexible bag is transferred to the rigid container for mixing with the other liquid or solution. The rigid container is evacuated and closed in a vacuum-tight manner after the one liquid or solution has been put into it, so that the liquid present in the flexible bag is sucked into the rigid container by the negative pressure prevailing in the rigid container as soon as a connection between the flexible bag and the rigid container is created by the special infusion set according to the invention. The negative pressure prevailing in the rigid container not only takes care of complete suction of the liquid from the flexible container but it also ensures mixing of the two liquids or solutions when they are in the rigid container, which can then be hung up in an inverted position like and orthodox infusion flask in order to administer the infusion solution formed in it to a patient in the usual manner.

As both the flexible bag and the rigid container are sealed in a sterile manner it is possible for the two liquids to be mixed together in a sterile manner immediately before they are administered. Accordingly it is possible to mix together in a simple and sterile manner two liquids, for example parenteral liquids, to be administered, without troublesome mechanical steps such as squeezing or shaking of plastics bags, fracture or rupture of separating walls, raising and shaking of containers and the like. There is also the possibility of deciding only directly before mixing, which solutions or components are to be mixed together because the flexible bag and the rigid container of the apparatus according to the invention are only finally inter-connected when the infusion set is inserted into their stopper closures.

Although the invention is described in connection with the mixing of two liquids to form a solution, it would also be possible to mix together more than two liquids, the vacuum-tight rigid container then having to have a sufficient volume to receive all the liquid components which are stored in a sterile manner in a corresponding number of flexible bags.

Preferably the rigid container is a glass flask such as is frequently used for infusions whilst the flexible bag is made of a thermoplastic synthetic resin, for example polyvinyl chloride.

The apparatus according the the invention is particularly suitable for glucose solutions and amino acids solutions which are to be mixed together to form an infusion solution. It is known to produce infusion solutions from such components and it is also known that glucose solutions and amino acid solutions have to be stored separately from one another before administration in order to prevent the so-called Maillard reaction between the hydroxyl groups of the glucose or of possibly another sugar such as for example fructose on the one hand and the amino groups of the amino acid.

As a rule the amino acid solutions comprise mixtures of different amino acids necessary for the organism, according to the kind of treatment being given to the patient. The amino acid solutions generally contain at least the eight so-called essential amino acids and if necessary histidin (e.g. in the case of kidney complaints). In a total parenteral treatment the amino acid solution can however also contain the so-called semi-essential/or non-essential amino acids. The concentration of the amino acids in the amino acid solutions generally lies in the range of about 0.5 to 30 g per 100 ml of solution. The lower limit frequently lies at about 3 g per 100 ml and the upper limit at about 20 g per 100 ml.

The concentration of the sugar solution, in particular a glucose solution, as a rule lies in the range of about 5 to 90 g per 100 ml of the sugar solution. The lower limit lies generally at about 20 g per 100 ml and the upper limit at about 85 g per 100 ml, the preferred solutions having a content of the order of magnitude of about 70 to 80 g per 100 ml of glucose. This is basically known to the expert (see Total Parenteral Nutrition in the Hospital and at Home; K. N. Jeejeebhoy, CRC Press Inc. Boca Raton, Fla., USA (1983)).

In the use of the apparatus according to the invention for storing and mixing glucose solutions and amino acid solutions the amino acid solution is put into the vacuum-tight closable rigid container, preferably the glass flask, as it has been found that amino acid solutions cannot be stored in plastics bags because of the danger that amino acid solutions are affected by the plastics and/or by the atmospheric oxygen which can penetrate through the plastics.

The rigid container, preferably an infusion flask made of glass, has a volume such that it can accept the entire mixture of liquids. It is generally filled up to somewhat more than half way with one of the components of the solution, such as the amino acid solution, under sterile conditions and then evacuated and sealed because normally a smaller quantity of glucose solution needs to be mixed with a larger quantity of amino acid solution. The volume of the rigid container can be somewhat greater than the volume of the liquid mixture to allow problem-free and uniform thorough mixing of the liquid components after the inter-connection has been made between the two containers which contain the individual liquid components. In addition the rigid container, namely for example the infusion flask, can be shaken after the liquid components have been brought together in order to improve the mixing. It is generally sufficient if the rigid container is inverted after the components have been brought together and is hung up in the inverted position in the usual manner for infusion flasks to be used for administering an infusion.

The injection needles of the infusion set according to the invention are provided for example with protective caps in order to keep them sterile before use. By removing the cap immediately before insertion into one of the stopper closures of the apparatus it it possible to achieve the result that even the connection between the two containers of the apparatus takes place under sterile conditions.

According to a further feature of the invention the flexible plastics bag can be fitted onto the rigid container in such a way that the two together form a transportable unit without them being put into communication, before such an interconnection is achieved with the aid of the infusion set according to the invention.

For this purpose the flexible bag is preferably formed so that it can be mounted on the rigid container, such as the infusion flask, like a rucksack in a so-called "piggyback" manner. The plastics bag can furthermore have a loop serving as a handle in order to allow the infusion flask, complete with the plastics bag mounted on it, to be lifted up with the outlet opening downwards and hung for example on a hook for the infusion period.

Figure 4:
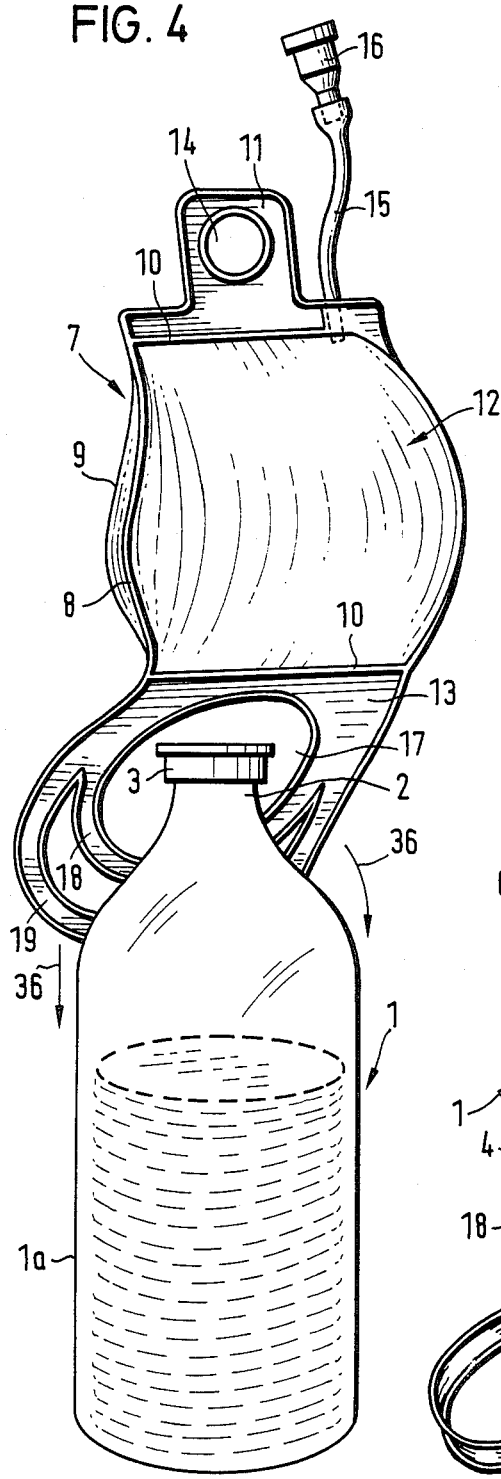
Figure 5:
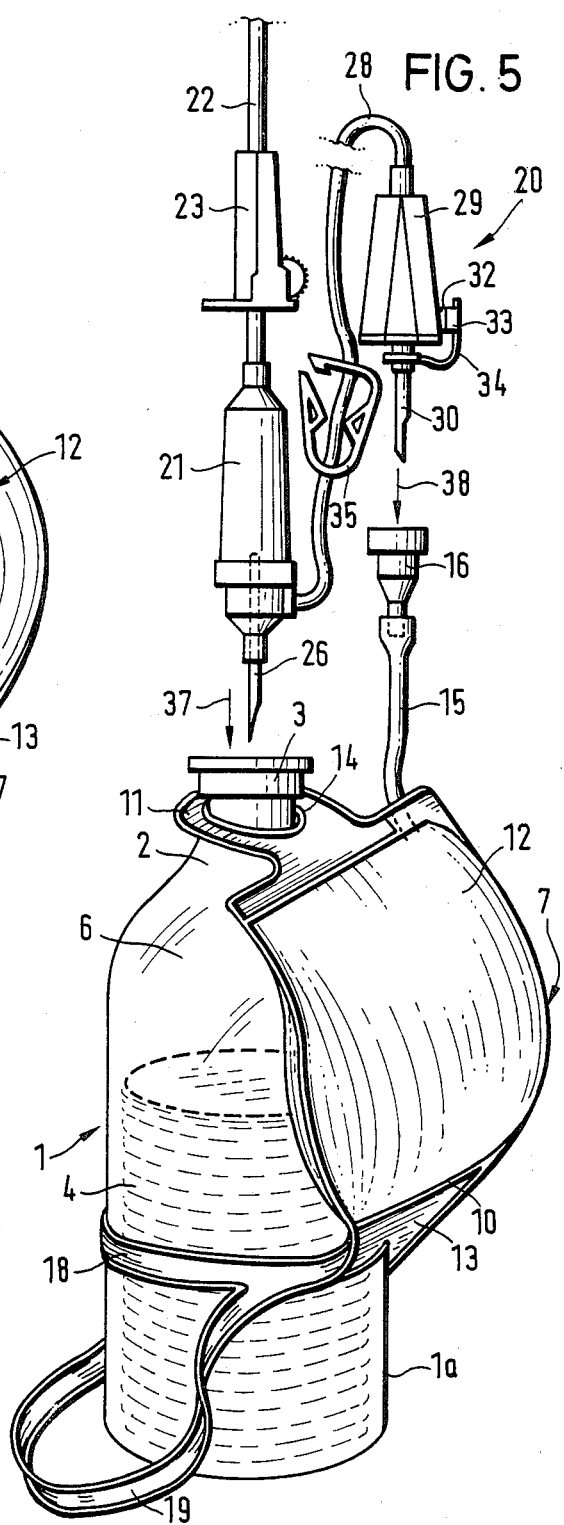
Figure 6:
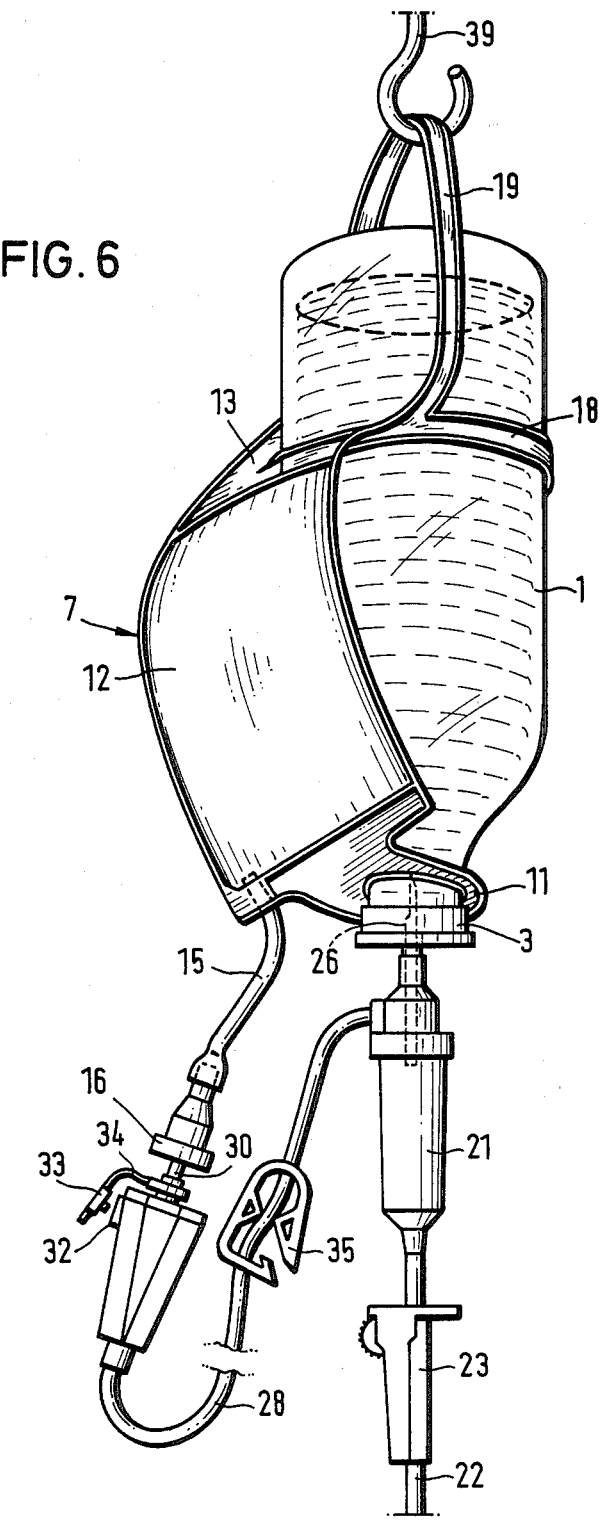

An embodiment of the apparatus according to the invention is illustrated by way of example in the drawings in which:

FIG. 1 is a perspective view of an infusion flask forming the rigid container of the apparatus and partially filled with one of the liquids to be mixed together, FIG. 2 is a plan view of the flexible plastics bag designed to receive a second liquid, FIG. 3 is an elevation of the special infusion set of the apparatus according to the invention, FIG. 4 is an elevation from which it can be seen how the plastics bag filled with the one liquid is mounted on the infusion flask which is partly filled with the other liquid, FIG. 5 is a perspective view of the infusion flask with the flexible plastics bag mounted on it in a "piggy-back" fashion and it can be seen how the infusion set according to the invention is connected to the infusion flask and the flexible bag and FIG. 6 is a perspective view of the apparatus according to the invention in its operating position in which the infusion solution mixing in the infusion flask is administered to a patient.

The rigid container 1 illustrated in FIG. 1 is an infusion flask made of glass with a reduced neck 2 on which a closure 3 is mounted, closing the infusion flask in an airtight and vacuum-tight manner, but which can be penetrated by an injection needle of an infusion set as further explained below.

The container 1 is filled somewhat more than half full with a liquid 4. In the upright position of the container 1 shown in FIG. 1, there is a space 6 present in the container 1 above the liquid level 5, and this space is evacuated after the liquid 4 has been put in and has a volume which is sufficient to receive the second liquid stored in the flexible plastics bag so that the two liquids are mixed together and form for example an infusion solution.

The flexible bag 7 illustrated in FIG. 2 is made of two thermoplastic synthetic resin sheets 8 and 9 which are permanently joined together along welded seams 10. The bag 7 is divided into three main portions 11, 12 and 13 by the welded seams 10.

The portion 11 is in the form of a tongue-shaped tag having an opening 14 which matches the reduced neck 2 of the rigid container 1.

The central portion 12 of the bag 7 serves to receive the second liquid which can be put into it through a tube 15. On the outer end of the tube 15 there is a closure 16 which, like the closure 3 on the container 1, can be penetrated by a needle of an infusion set in order to transfer the liquid in the central portion 12 of the bag 7 to the rigid container 1 to form the desired infusion solution.

The third portion 13 is again formed as a tag and contains an opening 17 which fits the main portion of the container 1 and embraces it with a ring-shaped web 18. Also the tag-shaped portion 13 is provided with an arcuate loop 19 serving as a handle and as a loop for hanging.

The infusion set 20 illustrated in FIG. 3 comprises a drop chamber 21, an infusion tube 22 connected to it with a flow regulator 23 mounted on it and a needle adapter 24 which is connected to the infusion tube 13 and which can be covered over in a sterile manner as shown in FIG. 3 by means of a removable protective cap 25.

An injection needle 26 is connected to the opposite end of the infusion tube 22 from the drop chamber 21 and it is covered in a sterile manner by a removable protective cap 27 as shown in FIG. 3.

A further flexible tube 28 is connected to the drop chamber 21 and is provided on its outer end with a closable air inlet filter 29. There is a further injection needle 30 on the outer end of the air inlet filter 29 and this is covered in a sterile manner by a removable protective cap 31 as shown in FIG. 3.

The air inlet filter 29 is provided with a lateral opening 32 closed in an airtight manner by means of a stopper cap 33 which is retained permanently on the lower end of the needle 30 by means of a loop 34.

A flow regulator 35 of an orthodox kind is mounted on the tube 28 and it can clamp the tube 28 to a greater or lesser extent in order to reduce the cross-section for flow if desired and thereby to allow restriction of the mean rate of flow.

From FIGS. 4 and 5 it can be seen how the flexible bag 7 is mounted on the rigid container 1. The tag-like portion 13 of the bag 7 is first drawn in the direction of the arrow 36 from above over the neck 2 of the container 1 so that the opening 17 fits over the reduced neck 2 of the container 1 and passes downwards onto the main portion 1a of the container 1 and finally it embraces it with the web 18 like a ring or collar. Then the portion 11 is fitted onto the neck 2 of the container 1 so that the neck projects through the opening 14 and the portion 11 lies below the closure 3 of the container 1, as shown in FIG. 5.

It can also be seen from FIG. 5 that the bag 7 is mounted on the flask-like container 1 like a ruckshack or back pack. The opening 17 in the tag-shaped portion of the bag 7 is dimensioned so that it makes a tight seating on the main portion 1a of the container 1 and embraces it firmly like a ring. The friction connection between the container 1 and the web 18 of the tag-shaped portion 13, even when the container 1 is a glass flask, is sufficiently firm to prevent a displacement of the container 1 with respect to the bag. On the contrary the container 1 with the bag 7 mounted on it can also be carried upside down and for this purpose the loop 19 is used as a handle. This is assisted by the fact that the opening 14 is only large enough to take the reduced neck 2 of the container 1 and accordingly the container cannot slip further through this opening.

FIG. 5 shows that the container 1 and the bag 7 form a relatively compact unit, the portion 12 of the bag being filled with a liquid which can be transferred to the container 1 with the aid of the infusion set 20 in the manner to be described below.

The container 1 with the bag 7 mounted on it is put in the position illustrated in FIG. 5. Then the protective caps are removed from the needles 26 and 30 in order to allow the needles to be inserted in the stopper closure 3 of the container 1 and the closure 16 of the tube 15 as indicated by the arrows 37 and 38 in FIG. 5. This results in a connection between the interior of the container 1 and the interior of the bag 7. Because of the negative pressure or vacuum present in the space 6 in the container 1 the liquid present in the portion 12 of the bag is sucked into the container 1 through the connection formed by the tube 28 until the bag 7 is practically empty. Then mixing takes place between the liquid 4 present in the container 1 and the liquid which has been sucked in.

The apparatus can now be used for administering an infusion. For this purpose it is grasped by the handle 19 and hung on a hook 39 on a stand, not shown in the drawing, or is secured at another point. The apparatus is put on its head so to speak and this causes a further mixing of the two liquids present in the container 1.

Now the protective cap 25 can be removed from the needle adaptor 24 and an infusion needle connected to it and applied to the patient in the usual way. Then it is only necessary to open the air inlet filter 29, for which purpose the cover 33 is removed from the opening 32 as shown in FIG. 6. This releases the negative pressure prevailing in the system up until then, so that the infusion liquid can drip from the container 1 and pass through the drop chamber 21 into the infusion tube 22.

The rate of infusion can be controlled by the drop regulator 23.

By means of the apparatus according to the invention it is possible to mix homogeneously together two or more liquids immediately before administration and to employ the container used for mixing directly as an infusion container or administration container without disconnecting the tube to the flexible bag and having to insert a separate infusion set which could give rise to sterility problems.

The flexible bag 7 is made approximately rectangular and is preferably made of two flexible plastics sheets welded together at their edges, further transverse welded seams defining the individual portions of the bag. In one embodiment of the invention the capacity of the central portion 12 of the bag 7 is about 250 to 300 ml. The tags and suspension means are made of the same material as the central portion 12 of the bag and in the embodiment illustrated by way of example they are extensions or components of the welded-together sheets.

The apparatus according to the invention can be used so that in practice in one sequence the two liquids are mixed together and then administered to a patient in the form of an infusion solution. During insertion of the needles into the stopper closures the infusion tube 22 is closed by the flow regulator 23. This regulator 23 is only opened after the venting valve 29 has been opened and the administration of the infusion liquid is to begin.

We claim:

1. An apparatus for handling and mixing together two liquids in a sterile manner comprising:
   a rigid container for housing a first fluid including a first closure disposed at one end of said rigid container;
   a flexible bag mounted to said rigid container for housing a second fluid, including a tube with a second closure mounted at one end of said tube;
   a first needle inserted into said first closure;
   a drop chamber fluidly connected to said first needle;
   an infusion tube fluidly connected to said drop chamber;
   a first flow regulation means disposed along said infusion tube for controlling the rate of fluid flow through said infusion tube;
   a second needle inserted into said second closure;

an air inlet filter fluidly connected to said second needle;

a connecting tube fluidly connecting said air inlet filter with said drop chamber;

a second flow regulation means for controlling the flow of said second fluid into said drop chamber, whereby insertion of said first and second needles in said first and second closures permits flow of the said first and second fluids to said drop chamber for mixing therein.

2. An apparatus as claimed in claim 1, wherein said flexible container further includes integral end flaps and a receiving means for attaching said flexible container to said rigid container.

3. An apparatus as claimed in claim 2, wherein said rigid container further includes a neck portion and a belly portion, and wherein said neck portion is disposed between said belly portion and said first closure.

4. An apparatus as claimed in claim 3, wherein said receiving means comprise receiving loops which are cut from said end flaps and are adapted to fasten to said neck portion and said belly portion.

5. An apparatus as claimed in claim 2, wherein said flexible container further includes an integral handle cut from one of said end flaps.

6. An apparatus as claimed in claim 5, wherein said handle is of a semi-circular shape.

7. An apparatus as claimed in claim 1, wherein said rigid container comprises a glass flask.

8. An apparatus as claimed in claim 1, wherein said rigid container comprises a container of a volume large enough to contain both of said fluids simultaneously.

9. An apparatus as claimed in claim 1, wherein said flexible container further includes a handle.

10. An apparatus as claimed in claim 1, wherein said air inlet filter includes a lateral opening, and a stopper cap for selectively covering said lateral opening.

11. An apparatus as claimed in claim 10, wherein said stopper cap is attached to said air inlet filter.

12. An apparatus as claimed in claim 1, wherein said first flow regulation means comprises an adjustable flow regulator.

13. An apparatus as claimed in claim 1, wherein said second flow regulation means comprises a cut-off device.

* * * * *